(12) United States Patent
Palmqvist et al.

(10) Patent No.: US 11,534,346 B2
(45) Date of Patent: Dec. 27, 2022

(54) ABSORBENT ARTICLE

(71) Applicant: Essity Hygiene and Health Aktiebolag, Gothenburg (SE)

(72) Inventors: Lisa Palmqvist, Gothenburg (SE); Anna Knös, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/640,202

(22) PCT Filed: Oct. 1, 2019

(86) PCT No.: PCT/SE2019/050943
§ 371 (c)(1),
(2) Date: Mar. 3, 2022

(87) PCT Pub. No.: WO2021/066686
PCT Pub. Date: Apr. 8, 2021

(65) Prior Publication Data
US 2022/0313497 A1    Oct. 6, 2022

(51) Int. Cl.
*B41F 3/24* (2006.01)
*A61F 13/15* (2006.01)
(Continued)

(52) U.S. Cl.
CPC .... *A61F 13/15764* (2013.01); *A61F 13/8405* (2013.01); *B41M 3/006* (2013.01); *D06P 5/00* (2013.01)

(58) Field of Classification Search
CPC ... B41F 5/24; B41F 3/24; B41F 17/00; B41M 3/006; B41M 1/18; A61F 13/84
See application file for complete search history.

(56) References Cited

U.S. PATENT DOCUMENTS

| 5,598,777 A | 2/1997 | Demoore et al. |
| 5,818,719 A | 10/1998 | Brandon et al. |

(Continued)

FOREIGN PATENT DOCUMENTS

| GB | 1141173 A | 1/1969 |
| WO | 2009126500 A1 | 10/2009 |

(Continued)

OTHER PUBLICATIONS

International Preliminary Report on Patentability (PCT/IPEA/409) dated Feb. 11, 2021, by the European Patent Office as the International Searching Authority for International Application No. PCT/SE2019/050943.

(Continued)

*Primary Examiner* — Tabassom Tadayyon Eslami
(74) *Attorney, Agent, or Firm* — Buchanan Ingersoll & Rooney PC

(57) ABSTRACT

A method for alignment of a pattern printed on a material for an absorbent article by a rotary printing device, including providing a first composition from a first chamber; providing a second composition including a detectable agent from a second chamber; wherein the first composition from the first chamber and the second composition from the second chamber are supplied to the same anilox roller or directly to the same rotary printing cylinder; and printing the first and second compositions on the material for an absorbent article by a rotary printing cylinder.

20 Claims, 1 Drawing Sheet

(51) Int. Cl.
*A61F 13/84* (2006.01)
*B41M 3/00* (2006.01)
*D06P 5/00* (2006.01)

(56) References Cited

U.S. PATENT DOCUMENTS

| | | | |
|---|---|---|---|
| 6,477,948 B1* | 11/2002 | Nissing | B42D 15/0093 |
| | | | 101/483 |
| 6,649,808 B1 | 11/2003 | Tao et al. | |
| 2003/0073966 A1 | 4/2003 | Sosalla et al. | |
| 2006/0016354 A1 | 1/2006 | Telljohann | |
| 2012/0222571 A1 | 9/2012 | Byrne et al. | |
| 2015/0290924 A1* | 10/2015 | Eriksson | B41F 3/56 |
| | | | 101/486 |
| 2016/0200095 A1 | 7/2016 | Pekurovsky et al. | |
| 2019/0001017 A1 | 1/2019 | Palmqvist et al. | |

FOREIGN PATENT DOCUMENTS

| | | |
|---|---|---|
| WO | 2013171366 A2 | 11/2013 |
| WO | 2017007398 A1 | 1/2017 |
| WO | 2019172769 A1 | 9/2019 |

OTHER PUBLICATIONS

International Search Report (PCT/ISA/210) with translation and Written Opinion (PCT/ISA/237) dated May 22, 2020, by the Japan Patent Office as the International Searching Authority for International Application No. PCT/SE2019/050943. (17 pages).

\* cited by examiner

ABSORBENT ARTICLE

TECHNICAL FIELD

The disclosure relates to a method for printing a material for an absorbent article.

BACKGROUND

Absorbent articles such as sanitary napkins, panty liners and diapers sometimes include colored regions to highlight various sections of the article such as the location of the absorbent core in the crotch part of the article. An ink may be printed on the topsheet material or any other material or layer of the article prior to the production of the article or may be printed in line. Topical additives such as lotions may be added to the article in order to provide a skin condition benefit for the user of the article. WO2017007398A1 discloses the addition of ink and additives by a rotary printing device such as by flexographic printing. Flexographic printing of skin beneficial agents/additives enables vast possibilities to add agents to materials for absorbent articles. The skin beneficial agents are to be located directly against the human body. There is still a need to improve the printing methods for the addition of additives to materials for absorbent articles.

SUMMARY

The present disclosure provides a solution for print synchronization for rotary printing devices in relation to materials for production of absorbent articles.

The invention concerns a method for alignment of a pattern printed on a material for an absorbent article by a rotary printing device according to claim 1. The method comprising providing a first composition from a first chamber; providing a second composition comprising a detectable agent from a second chamber; wherein the first composition from the first chamber and the second composition from the second chamber are supplied to the same anilox roller or directly to the same rotary printing cylinder; and printing the first and second compositions on the material for an absorbent article by a rotary printing cylinder.

The first and second chambers may be combined in one chamber with two separate compartments. The first and second chambers may be horizontally oriented in relation to the anilox roll. The first and second chambers may be vertically oriented in relation to the anilox roll and the outlets from the chambers may be horizontally orientated in relation to the anilox roll.

The rotary printing device may be a flexographic printer.

The anilox roll may be banded. A banded anilox roll may have different transfer volumes and/or line counts for the first and second compositions respectively. Areas with different transfer volumes and or line counts may be separated by an area/band without transfer.

The first composition may comprise a functional agent. The first composition may comprise a functional agent selected from a skin beneficial agent, an adhesive, a cooling or heat generating agent, an antimicrobial agent. The first composition may comprise a water emulsion of a skin beneficial agent. The first composition may comprise microcapsules. The first composition may comprise water-based ink. The first composition may comprise a mixture of any of the above.

The second composition may comprise a detectable agent that emits light in the UV or visible light spectra. The second composition comprising a detectable agent may also comprise the first composition as mentioned above.

The first and second compositions may be printed with different printing patterns. The first and second compositions may be printed with different frequencies.

The first composition may be printed >0.1 mm from a first edge of the material and up to and including 99% of the width of the material, such as 95%, such as 80% of the width of the material. The second composition may be printed >0.1 mm from a second edge of the material and up to and including 50% of the width of the material, such as less than 40%, such as less than 30%, such as less than 20% of the width of the material.

The detectable agent may form a sync mark. The size of the sync mark may be >0.1 mm, such as more than 1 mm and less than 50 mm. The size of the sync mark may be 10×20 mm.

The detectable agent may be detected by means of a sensor or camera. The material for the absorbent article may be converted by means of inline converting into an absorbent article for personal care use.

The method may further comprise an additional step of removing the sync mark, such by cutting off the edge part of the material comprising the sync mark.

The material for the absorbent article may be a nonwoven, airlaid, film, laminate, highloft nonwoven, cellulose tissue or a combination thereof.

DETAILED DESCRIPTION

The printing method according to the disclosure uses two chambers for the rotary printing device, or one chamber with two different compartments. The printing equipment, in case of a flexographic printer, uses the same anilox roller, cliché and printing cylinder for the printing method, however two different chambers to supply printing compositions to the same anilox roller. Chamber one may contain a composition that may comprise skin beneficial agents/additives and chamber two may comprise a composition comprising a detectable agent, such as a UV fluorescent ink, to form a detectable sync mark on a material for an absorbent article.

The printing method enables production of a material that will in most part contain the pattern of the first composition that may comprise skin beneficial agents/additives, but at least a transversal edge part of the material may comprise a composition comprising a detectable agent, such as an ink printed sync mark of UV fluorescent ink. The sync mark may aid in the further processing of the absorbent article to synchronize the parts of the material containing composition one, that may comprise additives, to predetermined locations on the absorbent article. An edge part of the nonwoven material carrying the detectable agent may later be removed during the processing of the article, if needed. Chamber two may comprise the same composition as ink chamber one which enables easy measurement and control of added amounts of the additives to the material, while not interfering with the part of the material destined for contact with the user of the absorbent article.

As used herein "beneficial agent" means a beneficial additive bringing a physical, medical, pharmacological, chemical, dermatological or emotional benefit to the user of the article.

According to one embodiment "beneficial agent" means a beneficial additive bringing a physical, medical, pharmacological, chemical, dermatological or emotional benefit to the user of the article other than delivered by a perfume or scent.

The beneficial agent may be a skin beneficial additive.

As used herein "absorbent article" means an article selected from a sanitary napkin, a panty liner, an incontinence pad, an incontinence diaper, feminine diaper, a belted diaper, baby diaper.

The compositions may comprise at least a binder and a beneficial agent. The compositions may further comprise an ink that may be a standard formulation known to the skilled man in the art. The ink may be water-based or solvent-based, which may include colored pigments or dyes or be colorless. The ink may also include typical printing additives well known to those skilled in the art such as solvents, co-solvents and processing aids. Solvent may include among other alcohols, esters, aldehydes and water. Binders may be, but are not limited to, polymers, resins, emulsions and mixtures based on styrenes, acrylates, acetates, alkydes, polyurethanes, nitrocellulose or other cellulose derivatives, polyglycols, polyvinylbutyrates, polyvinyl alcohols, polyvinyl pyrrolidone and derivatives or mixtures thereof. Constituents such as dispersants, surfactants, wetting aids, defoamers, anti-foaming agents, waxes, silicones, viscosity modifiers, pH regulators, anti-slip agents and preservatives may also be present in the ink formula together with one or more of the beneficial additives. The binder in the ink composition ensures the hardening of the ink.

The beneficial agent may be microencapsulated and added to the ink as an emulsion or as a powder. The concentration of microcapsules in the resulting ink composition and the amount of ink composition applied to the absorbent article may be determined by the skilled man in the art by routine experiments and formulated for each specific use. The concentration of microcapsules depends on the used beneficial agent and the desired effect of the article. The amount of ink applied to the absorbent article will depend on the composition of the ink and on the desired pattern on the article. The amount of ink needed may vary also depending on the surface absorbency.

The concentration of microcapsules on the article may be at least 0,001 $g/m^2$, or at least 0.01 $g/m^2$ or at least 0.1 $g/m^2$ and below 5 $g/m^2$, or below 1.0 $g/m^2$ or below 0.6 $g/m^2$. The concentration of microcapsules on the article may range between 0.001-5 $g/m^2$, or 0.01-1 $g/m^2$ or 0.05-0.6 $g/m^2$.

The size of any added microcapsules may be at least 1 µm, or at least 5 µm, or at least 10 µm and may be below 100 µm, or below 70 µm, or below 40 µm. The size of the microcapsules may range between 1-100 µm. The size of the microcapsules may be 5-70 µm. The size of the microcapsules may be 10-40 µm.

The technique of microencapsulation of additives is known for other uses such as cosmetics. Examples of companies producing such microcapsules are Devan Chemicals, Belgium; Encapsys, USA; Micro Capsule Technologies, France; and Robert Blondel, France, Salvona Technologies, USA.

Microencapsulation may be done through polymerization in oil-in-water emulsions to create dispersions or dry powders or water-in-oil emulsions. The microcapsule material may be of a material known to the skilled man in the art. Typical shell materials include polymeric, melamine, and silica based compositions. In one embodiment the microcapsule material is a composite of silicone and melamine polymers. The capsule material may be of natural origin such as alginate.

The beneficial agent may be selected from extracts from plants, herbs, fruits, seeds, spices and oils.

The beneficial agent may be a hydrophobic or lipophilic substance or additive.

The beneficial agent may be selected from almond oil, argan oil, sesame seed oil, jojoba oil, grapeseed oil, shea butter, olive oil, coconut oil, avocado oil, limonene, linalool, geraniol, citral, coumarin, hibiscus, *Lavendula augustifolia*, calendula, chamomile, peppermint, sandalwood, peach, mango, apricot, sea buckthorn, coffee, vanilla, chocolate, menthol, xylitol.

The beneficial agent may also be selected from carbamid, glycerin, dimethicone, tocopheryl (vitamin E), ascorbic acid (vitamin C), allantoin, thymol, salicylates.

An advantage of microencapsulation of beneficial agents is that agents that would otherwise be incompatible with the ink can be added and properly dispersed as microcapsules. A further advantage is that the release of the agent is gradual during the use of the article and the scent, if any, will be reduced in the manufacturing operation as well as on the shelf.

The compositions are applied by printing. By printing we herein mean a precise application of a fluid to form a coating or other dry layer on a substrate. By precise we mean that the medium will be placed in designated areas on the substrate, rather than in a poorly controlled fashion such as when using a spraying or extrusion technique. The print is by a rotary printing device, e.g. flexoprint, screen print or rotogravure. The printing techniques are further described in "Handbook of print media: technologies and production methods"/ed. Helmut Kipphan; Springer, 2001; ISBN 978-3-540-29900-4.

The compositions may be applied by a synchronized in-line print technique, such as by flexoprint, allowing for an exact placement of the compositions.

The steps of printing may be incorporated as inline steps in a process of manufacturing absorbent articles, or the layers may be printed off-line. It is also possible to print the layers before or during assembly of the components of the absorbent article.

After printing any solvents will evaporate so that the composition dries almost instantaneously. However, a drying step may be added, such as blowing hot air on the printed surface.

The compositions may be applied in selected areas as desired, and in any desired pattern. The present method allows very accurate patterns and fine lines and dots to be formed.

When arranged in the absorbent article, the top sheet has body facing surface and a garment facing surface. The compositions may be applied to one or both of said surfaces. By applying the ink compositions on the body facing surface the user obtains a direct access to beneficial agents.

Depending on the location of the composition various advantageous functional effects can be obtained. Examples of patterns of with different functions are given below. These patterns can be used individually but may of course advantageously be combined to achieve the desired characteristics of the absorbent article.

The composition may be printed on an area or zone of the article selected from:
 along longitudinal side edges of the crotch portion;
 a central area of the crotch portion;
 a central area of the front portion;
 a central area of the back portion.

The absorbent article may further comprise a wing extending from each longitudinal side edge of the article and the composition may be printed on an area of said wings.

The printed areas or zones may be an area or zone having an oval, circular, moon, heart, arrow shape etc. and placed in certain regions of a product to give a unique function.

The absorbent article comprises at least a topsheet layer and if desired also a backsheet layer and an absorbent layer arranged between the topsheet and the backsheet layers. Each layer of the absorbent article has a garment facing surface and a body facing surface, and the compositions may be applied to any of said surfaces. The composition may be added to an acquisition layer located beneath a topsheet.

Detectable agents may be an ink such as a waterbased ink, optical brighteners, optical brightening agents (OBAs), fluorescent brightening agents (FBAs) or fluorescent whitening agents (FWAs).

The absorbent article may comprise a body facing topsheet of a nonwoven, a film or a laminate thereof or a foam and a back sheet of a liquid impervious polymeric film material or a laminate of a film and a nonwoven material and an absorbent layer comprising pulp and/or superabsorbent material and/or a fibrous web.

The backsheet material may be breathable or non-breathable. The back sheet is facing away from the user during use and is opposite to the body facing topsheet layer of the absorbent article. A fastening means may be applied on the garment facing side of the back sheet, which may be covered by a release paper or single wrap.

Activation of microcapsules may be performed by mechanical activation wherein the capsule breaks up by a shearing force or by pressure upon contact. When the absorbent article is used the microspheres will break due to the user's movements. Not all microcapsules will break at the same time as some may be buried further down in the material and there will thus be a slow, continuous and beneficial release of the agent during use of the article. A long-lasting effect may thus be achieved.

Other means of activating microcapsules in addition to mechanical rupture are e.g. change of pH, dissolution, temperature change, osmosis, photolytic release, ultrasonication, biodegradation, diffusion and erosion.

The application by print allows for a precise placement of a delicate printed pattern in chosen areas on the article, compared with when an additive is applied for example as a constituent of the spin finish on a topsheet, in a so-called cocktail, which is commonly used by nonwoven suppliers.

BRIEF DESCRIPTION OF THE DRAWINGS

The disclosure will be described in greater detail below with reference to the figures and examples shown, wherein FIG. 1 discloses a rotary printing device according to the disclosure.

In FIG. 1 the first and second chambers 3,4 are vertically oriented in relation to the anilox roll 6 and the outlets from the chambers horizontally orientated in relation to the anilox roll (not shown). The first and second chambers 3, 4 may also be horizontally oriented in relation to the anilox roll.

FIG. 2 discloses a material 8 for an absorbent article with a print 9 of a composition comprising a functional agent and a separate synchronization print 10 comprising the same composition but also comprising an UV brightener.

EXAMPLES

Figure 1:
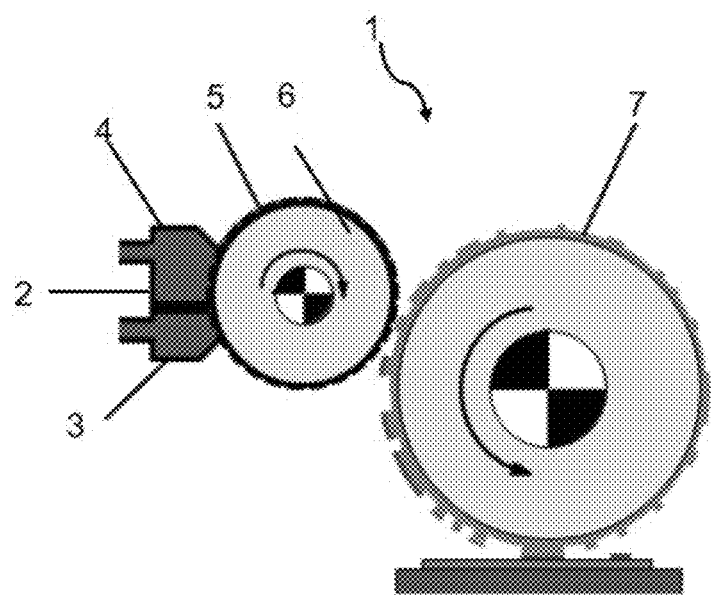
FIG. 1 discloses a rotary printing device 1 in the form of a flexographic printer. Two chambers 3, 4 or a chamber 2 with two separate compartments 3, 4 supply printing compositions to an anilox roll 6 having a cliché 5 thereon with the pattern to be printed on the material located on the plate cylinder 7.
Figure 2:
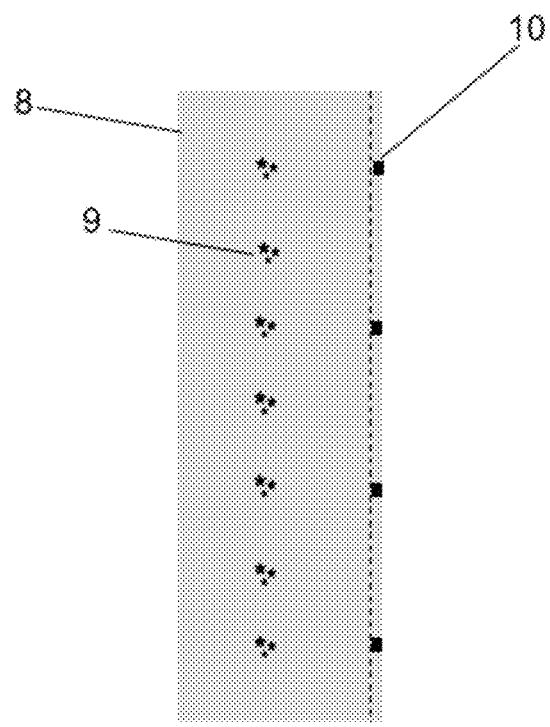
FIG. 2 discloses a material for an absorbent article printed with composition one and two according to the disclosure.

Amounts are given by weight unless otherwise stated below.

Example 1

0.1% of Uvitex NFW UV brightener (Ciba Specialty Chemicals, NL) was added to a microcapsule emulsion containing 35% of active matter of shea butter (no. 6573, Micro Capsule Technologies, France) upon continuous mixing by agitator for 30 min at ambient temperature. The resulting mixture was added to one chamber in connection with a flexographic printer. The same type of microcapsule emulsion without UV brightener was added to a second chamber on the same flexographic printer. Both mixtures were then applied onto different areas of a web of nonwoven with a surface weight of 20 g/m$^2$ by means of synchronized flexoprinting at 300 m/min using the same anilox and cliché for both mixtures coming from the two chambers, followed by drying in hot air and subsequent inline lamination to acquisition layer, core and backsheet materials to form a personal care product for hygiene use. A UV sensor (Keyence, JP) was used to detect the position of the printed pattern with UV brightener to align it to the product, and thereby also align the pattern without UV brightener printed with the same cliché.

Example 2

0.25% of MPI Bright 100 UV brightener (MPI-Chemie, NL) was added to a microcapsule emulsion containing 42% of active matter of almond oil (Captex Amande douces no. 20005, Robert Blondel, France) upon continuous mixing by agitator for 30 min at ambient temperature. The resulting mixture was added to one compartment of a divided chamber in connection with a flexographic printer. The same type of microcapsule emulsion without UV brightener was added to the other compartment of the divided ink chamber. Both mixtures were then applied onto different areas of a web of spunbond nonwoven with a surface weight of 15 g/m$^2$ by means of synchronized flexoprinting at 400 m/min using the same anilox and cliché for both mixtures coming from the two separated compartments, followed by drying in hot air and subsequent inline converting into a personal care product for hygiene use. A UV sensitive vision camera (Accusentry, US) was used to detect the position of the printed pattern with UV brightener to align it to the product, and thereby also align the pattern without UV brightener printed with the same cliché before removing the material part printed with UV brightener in the final product shape cut.

Example 3

An aloe vera solution with 90% active matter (CCS, Sweden) was added to one chamber in connection with a flexographic printer. A waterbased ink (Kappaflex 96-3670, Kapp Chemie, Germany) was added to another chamber. Both fluids were then printed onto different areas of a web of carded nonwoven with a surface weight of 21 g/m$^2$ by means of synchronized flexoprinting at 300 m/min using the same anilox and cliché for both mixtures coming from the two chambers, followed by drying in hot air and subsequent inline converting into a personal care product for hygiene use. A sensor (SICK, Germany) was used to detect and align the printed color pattern to the correct position in the product and thereby also aligning the transparent aloe vera pattern printed with the same cliché, before removing the material part printed with color ink in the final product shape cut.

The invention claimed is:

1. A method for alignment of a pattern printed on a material for an absorbent article by a rotary printing device, comprising:
   a. providing a first composition from a first chamber;
   b. providing a second composition comprising a detectable agent from a second chamber;
   c. wherein the first composition from the first chamber and the second composition from the second chamber are supplied to a same anilox roller or directly to a same rotary printing cylinder;
   d. and printing the first and second composition on the material for an absorbent article by a rotary printing cylinder;

wherein the first composition comprises a functional agent selected from a skin beneficial agent, an adhesive, a cooling or heat generating agent, or an antimicrobial agent; and wherein the second composition comprises a detectable agent that emits light in the UV fluorescent or visible light spectra; and wherein the second composition also comprises the first composition.

2. The method according to claim 1, wherein the first and second chambers are combined in one chamber with two separate compartments.

3. The method according to claim 1, wherein each chamber has an outlet for supplying composition to the anilox roller or rotary printing cylinder.

4. The method according to claim 1, wherein the first and second chambers are horizontally oriented in relation to the anilox roll.

5. The method according to claim 1, wherein the first and second chambers are vertically oriented in relation to the anilox roll and wherein the outlets from the chambers are horizontally orientated in relation to the anilox roll.

6. The method according to claim 1, wherein the rotary printing device is a flexographic printer.

7. The method according to claim 1, wherein the anilox roll is banded.

8. The method according to claim 1, wherein a banded anilox roll has different transfer volumes and/or line counts for the first and second compositions respectively.

9. The method according to claim 8, wherein the areas with different transfer volumes and or line counts are separated by an area/band without transfer.

10. The method according to claim 1, wherein the material for the absorbent article has a first and a second transversal edge.

11. The method according to claim 1, wherein the first composition may be printed >0.1 mm from a first edge of the material and up to and including 99% of the width of the material.

12. The method according to claim 11, wherein the second composition is printed >0.1 mm from a second edge of the material and up to and including 50% of the width of the material.

13. The method according to claim 1, wherein the method further comprises an additional step of removing a sync mark.

14. The method according to claim 1, wherein the first and second compositions are printed with different printing patterns.

15. The method according to claim 1, wherein the first and second compositions are printed with different frequencies.

16. The method according to claim 1, wherein the first and/or second compositions comprise microcapsules.

17. The method according to claim 1, wherein the first and/or second compositions comprise a water emulsion of a skin beneficial agent.

18. The method according to claim 1, wherein the first and/or second compositions comprise water-based ink.

19. The method according to claim 1, wherein the material for the absorbent article is a nonwoven, airlaid, film, laminate, highloft nonwoven, cellulose tissue or a combination thereof.

20. The method according to claim 1, wherein the absorbent article is a feminine or light incontinence napkin or pad.

* * * * *